US00PP30090P3

(12) United States Plant Patent
Wezelenburg, Jr.

(10) Patent No.: US PP30,090 P3
(45) Date of Patent: Jan. 15, 2019

(54) ***ACER* PLANT NAMED 'JWW8'**

(50) Latin Name: *Acer palmatum*
Varietal Denomination: JWW8

(71) Applicant: Jan-Willem Wezelenburg, Jr., Hazerswoude-Dorp (NL)

(72) Inventor: Jan-Willem Wezelenburg, Jr., Hazerswoude-Dorp (NL)

(73) Assignee: JAN-WILLEM WEZELENBURG BOSKOOP, B.V., Hazerswoude-Dorp (NL)

( * ) Notice: Subject to any disclaimer, the term of this patent is extended or adjusted under 35 U.S.C. 154(b) by 0 days.

(21) Appl. No.: 15/731,647

(22) Filed: Jul. 12, 2017

(65) Prior Publication Data

US 2018/0027713 P1 Jan. 25, 2018

(30) Foreign Application Priority Data

Jul. 20, 2016 (QZ) ..... PBR 2016/1822

(51) Int. Cl.
*A01H 5/00* (2018.01)
*A01H 5/12* (2018.01)
*A01H 5/04* (2018.01)

(52) U.S. Cl.
USPC ..... Plt./224
CPC ..... *A01H 5/12* (2013.01); *A01H 5/04* (2013.01)

(58) Field of Classification Search
USPC ..... Plt./216, 224
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Acer palmatum*, 'JWW8', that is characterized by its broad vase-shaped plant habit, and its leaves that are an intense red-pink color in spring, changing to light orange-brown and changing to green in summer, and second summer shoots that are red in color.

2 Drawing Sheets

Botanical classification: *Acer palmatum.*
Variety denomination: 'JWW8'.

BACKGROUND OF THE INVENTION

The present invention relates to a new and distinct cultivar of *Acer palmatum*, and will be referred to hereafter by its cultivar name, 'JWW8'. 'JWW8' is a deciduous tree grown for use as a landscape plant.

The new cultivar originated as a chance seedling growing in a production field of *Acer palmatum* at a nursery in Hazerswoude-Dorp, The Netherlands in May of 2013. The parent plants are unknown as the field was planted with seeds collected and pooled from various unnamed open pollinated plants of *Acer palmatum.*

Asexual reproduction of the new cultivar was first accomplished by grafting by the Inventor in Hazerswoude-Dorp, The Netherlands in May of 2014. Asexual propagation of 'JWW8' by grafting has shown that the unique features of the new cultivar are stable and are reproduced true to type in successive generations.

SUMMARY OF THE INVENTION

The following traits have been repeatedly observed and represent the characteristics of the new cultivar. These attributes in combination distinguish 'JWW8' as a new and unique cultivar of *Acer.*

1. 'JWW8' exhibits a broad vase-shaped plant habit.
2. 'JWW8' exhibits leaves that are an intense red-pink color in spring, changing to light orange-brown and changing to green in summer, and second summer shoots that are red in color.

'JWW8' be compared to the *Acer* cultivars 'Kiyohime' (not patented) and 'Murasaki-kiyohime' (not patented). 'Kiyohime' is similar to 'JWW8' in being the same overall plant shape. 'Kiyohime' differs from 'JWW8' in having spring leaves that are orange-green in color with hints of red. 'Murasaki-kiyohime' differs from 'JWW8' in having a globe-shaped plant habit and spring leaves that are dark green in color with hints of purple.

BRIEF DESCRIPTION OF THE DRAWINGS

The accompanying colored photographs illustrate the overall appearance and distinct characteristics of a two-year-old plant of the new cultivar as grown in a greenhouse in a 19-cm container in Hazerswoude-Dorp, The Netherlands.

Figure 1:
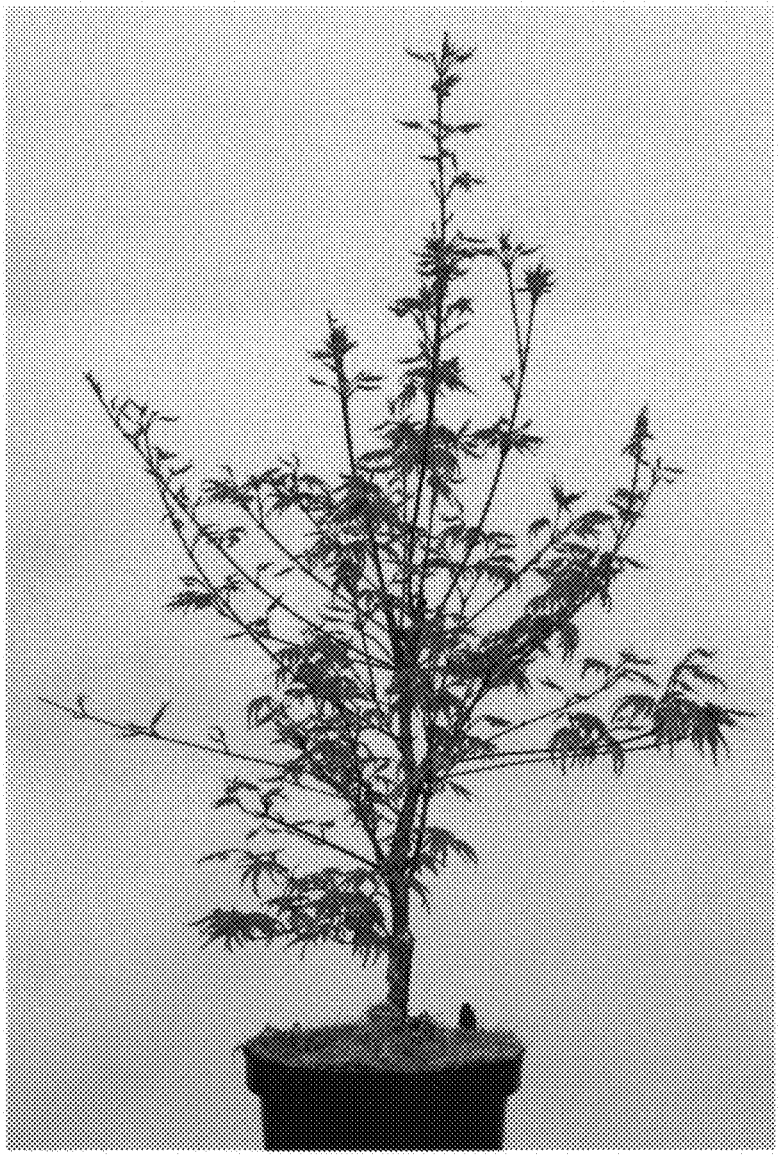
FIG. 1 provides an overall view of the foliage and plant habit of 'JWW8'.
Figure 2:
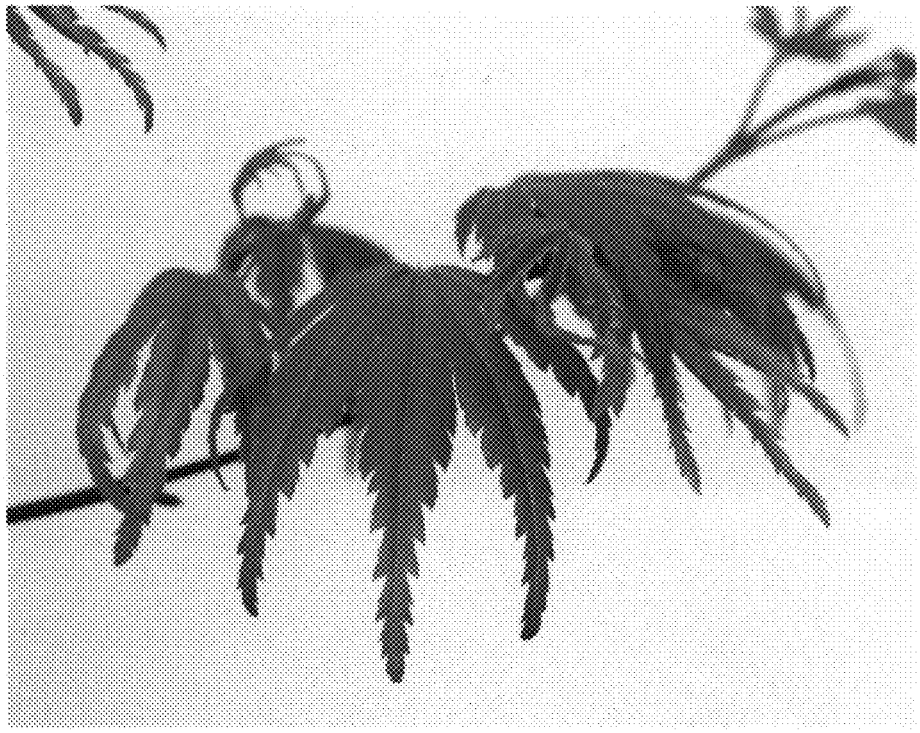

The photograph in FIG. 2 provides a close-up view of the young foliage of 'JWW8'.

Figure 3:
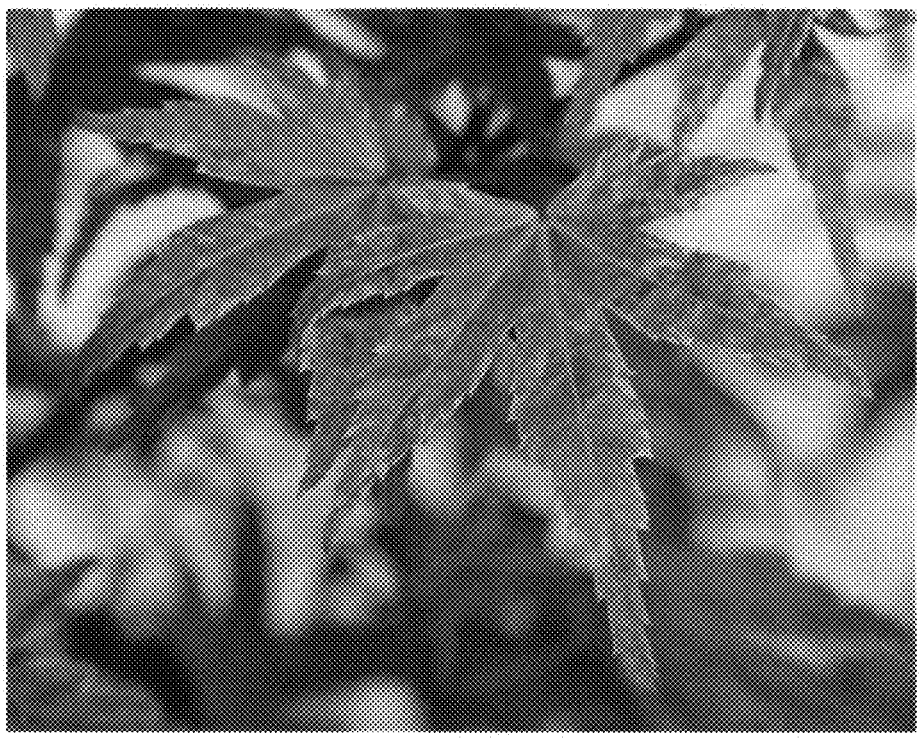

The photograph in FIG. 3 provides a close-up view of the mature foliage of 'JWW8'.

The colors in the photographs may differ slightly from the color values cited in the detailed botanical description, which accurately describe the colors of the new *Acer.*

DETAILED BOTANICAL DESCRIPTION

The following is a detailed description of a two-year old plant of the new cultivar as grown in a greenhouse in a 19-cm container in April in Hazerswoude-Dorp, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Deciduous tree.

*Plant habit.*—Broadly vase-shaped.

*Height and spread.*—An average of 200 cm in height and 150 cm in spread as a mature plant in the landscape, an average of 71 cm in height and 47 cm in width as a 2 year-old plants in a 19-cm container.

*Hardiness.*—At least in U.S.D.A. Zones 6 to 9.

*Diseases.*—No susceptibility or resistance to diseases has been observed.

*Root description.*—Fibrous, freely branched.

*Propagation.*—Grafting.

*Crop time.*—An average of 14 months to produce a young plant.

*Growth rate.*—Not highly vigorous.

Branch description:

*Stem shape.*—Round.

*Stem color.*—Young shoots; 183B to 183C, young branches; between 143A and 141A, flushed with 177A and 165A, older mature branches and bark; between 143A and 141A, 152B to 152C, fading to 199A with age, bark is 199D to 172A to 177B.

*Stem size.*—Lateral branches; 27.1 cm in length, 2 mm in diameter, main stem; 30 cm in length and 3 cm in width at soil line.

*Stem surface.*—Texture and luster; young branches; slightly glossy, glabrous, mature branches; slightly glossy and very lightly covered with lenticels; an average of 2 to 5 per square cm, 0.5 mm in length, less than 0.5 mm in width, 156D in color, main branch older bark; slightly glossy and slightly exfoliating and bark-like, lightly covered with lenticels; an average of 5 to 10 per square cm, 1 mm in length, 0.75 mm in width, 156D in color.

*Stem strength.*—Strong.

*Stem aspect.*—An average angle of 40° to vertical.

*Internode length.*—An average of 3.8 cm.

*Branching.*—Well-branched, 1 main stem and 30 secondary branches per main branch.

Foliage description:

*Leaf shape.*—Palmately lobed, orbicular in outline.

*Leaf division.*—Simple.

*Leaf base.*—Truncate.

*Leaf apex.*—Narrow acute.

*Leaf fragrance.*—None.

*Leaf venation.*—Palmate, upper surface color ranges between 146D and N199A, lower surface color is between 146D and 199A.

*Leaf quantity.*—An average of 16 (8 pairs) per lateral branch.

*Leaf margins.*—Palmately lobed, lobe margins serrate to bi-serrate, sinus depth medium to deep, sinus orientation is convergent.

*Leaf arrangement.*—Opposite.

*Leaf aspect.*—Flat, leaves in an average angle of 40° to lateral branch.

*Leaf attachment.*—Petiolate.

*Leaf surface.*—Texture of both surfaces glabrous and smooth, luster of both surfaces is slightly glossy, lower main veins are sparsely to moderately covered with very small, thin pubescence.

*Leaf size.*—Up to 5 cm in length and 4.9 cm width.

*Leaf color.*—Young leaves upper surface; 178B to 178C and 185A, young leaves lower surface; 177B and 184B, mature and fall leaves upper surface; 143A with blotches of 51D at the margins, mature and fall leaves lower surface; between 138A and 143A with blotches of 52D at the margins.

*Petioles.*—Up of 2.2 cm in length and 0.75 mm in width, texture is smooth and glabrous with moderately glossy luster, upper surface color 179A to 179C, lower surface 180D, fading to 179C.

*Stipules.*—None.

Inflorescence description: No flowers have been produced to date.

Fruit and seed: None produced to date.

It is claimed:

1. A new and distinct cultivar of *Acer palmatum* tree named 'JWW8' as herein illustrated and described.

* * * * *